United States Patent
Schliemann et al.

(10) Patent No.: US 9,592,334 B2
(45) Date of Patent: Mar. 14, 2017

(54) PRE-FILL SYRINGE

(75) Inventors: Eric Schliemann, Steisslingen (DE); Karl-Heinz Fuchs, Radolfzell (DE)

(73) Assignee: Stevanato Germany GmbH, Bad Oeynhausen (DE)

(*) Notice: Subject to any disclaimer, the term of this patent is extended or adjusted under 35 U.S.C. 154(b) by 64 days.

(21) Appl. No.: 13/042,796

(22) Filed: Mar. 8, 2011

(65) Prior Publication Data

US 2011/0224643 A1 Sep. 15, 2011

(30) Foreign Application Priority Data

Mar. 10, 2010 (DE) .................. 10 2010 010 967

(51) Int. Cl.
 A61M 5/00 (2006.01)
 A61M 5/315 (2006.01)
 A61M 5/28 (2006.01)
 A61M 5/31 (2006.01)

(52) U.S. Cl.
 CPC ............ *A61M 5/002* (2013.01); *A61M 5/315* (2013.01); *A61M 5/31511* (2013.01); *A61M 5/282* (2013.01); *A61M 5/3156* (2013.01); *A61M 5/31513* (2013.01); *A61M 2005/3112* (2013.01)

(58) Field of Classification Search
 CPC A61M 5/3156; A61M 5/31511; A61M 5/282; A61M 2005/3112; A61M 5/315; A61M 5/31513; A61M 5/31505; A61M 5/002
 USPC ........ 604/207–211, 219, 220, 221, 226, 181, 604/187
 See application file for complete search history.

(56) References Cited

U.S. PATENT DOCUMENTS

| | | | |
|---|---|---|---|
| 2,607,341 A | | 8/1952 | Brown |
| 2,725,057 A | * | 11/1955 | Lockhart ....................... 604/193 |
| 2,728,341 A | * | 12/1955 | Roehr ..................... A61M 5/28 206/365 |
| 2,941,530 A | * | 6/1960 | Laub ................. A61M 5/31513 604/219 |
| 3,107,785 A | | 10/1963 | Roehr |
| 3,584,626 A | * | 6/1971 | Johansson ............... A61M 5/00 604/193 |
| 3,890,956 A | * | 6/1975 | Moorehead .......... A61B 5/1405 600/578 |
| 4,184,953 A | | 1/1980 | Dorr |
| 5,067,947 A | * | 11/1991 | Volk ........................ A61M 5/24 604/110 |
| 7,083,596 B2 | * | 8/2006 | Saied ........................... 604/110 |
| 7,901,384 B2 | * | 3/2011 | Kleyman ........... A61M 5/31595 604/207 |
| 2005/0131313 A1 | * | 6/2005 | Mikulka et al. .............. 600/567 |
| 2007/0148326 A1 | * | 6/2007 | Hastings et al. ............. 427/2.27 |

FOREIGN PATENT DOCUMENTS

EP 1627605 B1 * 12/2010

* cited by examiner

*Primary Examiner* — Emily Schmidt
*Assistant Examiner* — Lauren M Peng
(74) *Attorney, Agent, or Firm* — Bachman & LaPointe, PC

(57) ABSTRACT

A pre-fill syringe with a receiver tube (1, 12, 21) with a nozzle (4, 20) positioned at the nozzle-side end of the receiving tube (1, 12, 21), the piston (2, 18) is to be formed in such a manner that it for a transport state at the nozzle-side end of the receiver tube (1, 12, 21) can be connected with the receiving tube.

16 Claims, 4 Drawing Sheets

PRE-FILL SYRINGE

BACKGROUND OF THE INVENTION

The present invention is drawn to a pre-fill syringe.

As state of the art technology, various so-called pre-fill syringes are known. Their disadvantage, however, is that, due to the medium inside the syringe body, the piston belonging to the syringe cannot be kept inside the syringe body, but is usually transported in such a manner that the piston lies in a position extracted from the syringe body and the user then activates the piston by pressing it down, thus pressing the medium out of the syringe body. The extracted piston requires packaging, which is costly and at the same time cumbersome because of the space required during transport.

SUMMARY OF THE INVENTION

A pre-fill syringe is distributed to the users pre-filled with a fluid. Though the fluid foremost and mainly needs to meet medical requirements, it is, however possible to satisfy cosmetic requirements with the fluid as well.

The transport state is preferably a state in which the pre-fill syringe in accordance with the invention is commonly packaged by the manufacturer and distributed to the user. A functional state is preferably a state in which the pre-fill syringe is activated by a user.

The pre-fill syringe consists of a receiving tube with a nozzle and a piston. The piston should preferably be formed in such a manner that in its transport state it is inserted over the end of the receiving tube on said tube's nozzle side. In this instance there is an advantage in the fact that, due to this connection by insertion, a savings in terms of space is achieved, since conventional pre-fill syringes need to be sent to the user with an extracted piston, in order to be able to send the fluid along with the syringes.

In a preferred embodiment, sections of the piston can protrude through the nozzle also into the interior of the receiving tube. Likewise, the same parts can serve to keep the nozzle of the receiving tube shut during the transport state.

In addition, the piston is to be formed in such a manner that in its functional state it at least partially can be pushed into the receiving tube. Functional state in this instance refers to the ejecting of the fluid out of the pre-fill syringe. This can occur in one single process or in several steps. The advantage lying herein is that the piston in its transport state for the time being is fixed on to the end on the nozzle side, thus saving space, and the user, to eject the fluid, can push the piston, in its functional state, at the area showing away from the end on the nozzle side, into the receiving tube.

In this instance, the piston can close during the transport state and open during functional state. It is also possible that the piston may be either set on to or inserted into the receiving tube several times in an alternating fashion either on the nozzle-side end or on the end showing away from nozzle-side end.

In a preferred embodiment, the circumference of the piston shall be variable. While in transport state the piston is to have a larger circumference than the receiving tube and while in functional state, the piston is to have a smaller circumference than the inner circumference of the receiving tube and is to be able to slide into the receiving tube either completely or partially. This makes it possible to achieve the advantage of saved space.

A preferred embodiment has a sealing in the interior of the receiving tube. This sealing, on the one hand, prevents in an advantageous manner the fluid from emitting from the side showing away from the nozzle-side end. In addition, the sealing functions together with the piston while in functional state. Additionally, it has a coupling which is able to receive the piston in functional state. This contributes further to the advantage of savings in terms of space, since during transport state the piston is no longer required to close the end showing away from the nozzle-side end.

In a preferred embodiment, the receiving tube has a groove on its inner side. This groove can run in phases, linearly or in a concentric arch. It provides the advantage that, when the user activates the syringe, and is, say, at the same time proportioning, in the phased embodiment fluid is ejected out of the nozzle only up to the end of a section extending straight downwards, and when the piston touches a vertically extending spot, the ejection of fluid is discontinued and the user is required firstly to turn the piston in the direction of the vertically extending groove. This turning movement needs to be continued until the user again hits upon a groove extending straight downwards and then may eject the next dose of the fluid from the receiving tube. The term top in this context refers to the end showing away from the nozzle-side end and the term bottom to the nozzle-side end.

The piston or an area of the sealing, in a preferred embodiment, has a curved cam which functions together with the groove. This curved cam serves to make sure that the user can only set the piston in motion along the groove and in accordance with proper use. This provides the advantage that even untrained staff can administer correct doses of the fluid.

In another preferred embodiment, the receiving tube has a handling dent. This handling dent has the advantage that the user can hold the receiving tube during functional state. Since the piston is shoved over the receiving tube, ring, which in the current state of the art has been formed for this purpose at the end showing away from the nozzle-side end, is missing. This provides the advantage that the user, thanks to the handling dent, has a secure hold against the pressure of the piston in functional state.

BRIEF DESCRIPTION OF THE DRAWINGS

Further advantages, features and details of the invention may be inferred from the below following description of preferred embodiments as well as from the drawings; said drawings show in.

DETAILED DESCRIPTION

Figure 1:
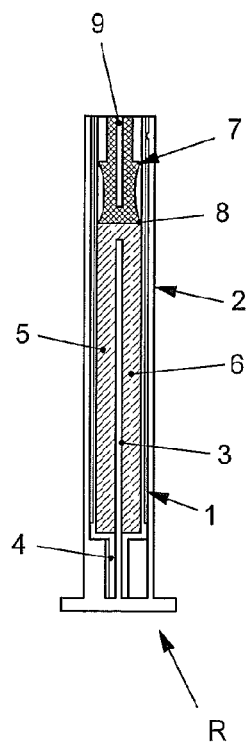
FIG. 1 an embodiment in accordance with the invention of a pre-fill syringe in transport state.

In FIG. 1, a pre-fill syringe R, in accordance with the invention, is shown. Here we are dealing with a cutaway side view. In the drawing in question, it is quite clear how the piston 2 is positioned around the receiving tube 1. This piston 2 protrudes with a section 3 through the nozzle 4 of the receiving tube 1 into the filling area 5 of the receiving tube. In this filling area 5, a medium 6 has been filled in. In addition, a sealing member 7 can be discerned. This sealing member 7 has, on its side showing towards the fluid 6, at least one sealing lip 8. In addition, a coupling 9 is shown in the sealing member 7.

Figure 2:
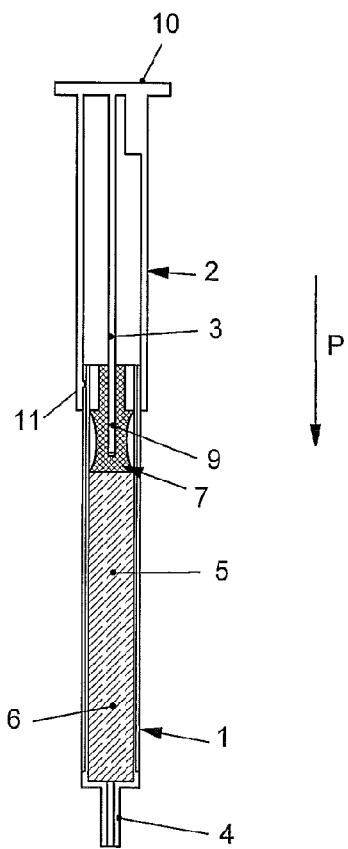
FIG. 2 the embodiment within the scope of the invention in accordance with FIG. 1 in functional state.

Now, FIG. 2 shows how the piston 2 is set from above on to the receiver tube 1. In this instance the piston 2 encompasses the circumference of the receiver tube 1. The section 3 is at this junction inserted into the coupling 9 of the sealing member 7. Now, as soon as the user presses on a pressing point 10 of the receiver tube 1 section 3 activates the sealing member 7 and moves it in the direction of the arrow P. Through this process it will press the medium 6, which is contained in the receiver chamber 5, through the nozzle 4.

Figure 3:
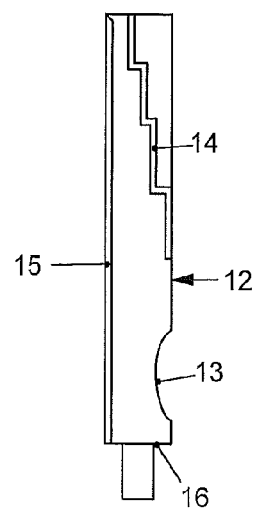
FIG. 3 an embodiment of a receiving tube in accordance with the invention.

Additionally, in FIG. 2 a curved cam 11 is shown. In this context, FIG. 3 is made reference to. FIG. 3 shows a further embodiment of a receiver tube 12 in accordance with the invention. This receiver tube 12 is formed to contain a handling dent 13. In addition, on the inner side of the receiver tube 12, a groove 14, extending in phases, or a groove 15, extending linearly, is shown. Even though the groove 14 extending in phases in FIG. 3 is not shown to extend all the way to the bottom 16 of the receiver tube 12, this may be inferred to be the case.

The curved cam shown in FIG. 2 serves to enable the user to activate the syringe along a straight groove 15 or along a phased groove 14 in the direction of the arrow P.

In this instance 11 takes a hold in the pertaining groove 14 or 15 and the user presses on the location surface 10 in the direction of the arrow P, in which instance the sealing member 7 is then led downwards along the pertaining groove 14 or 15.

The phased groove 14 would in this instance provide the advantage that an ejection of the fluid 6 in doses would be made possible. When the curved cam 11 takes hold in the linearly extending groove 15, the user could eject all the fluid 6 out of the receiver tube 12 in one movement. The receiver tube shown in FIG. 3 can be activated by a piston in the same manner, as is the case with receiver tube 1.

Figure 4:
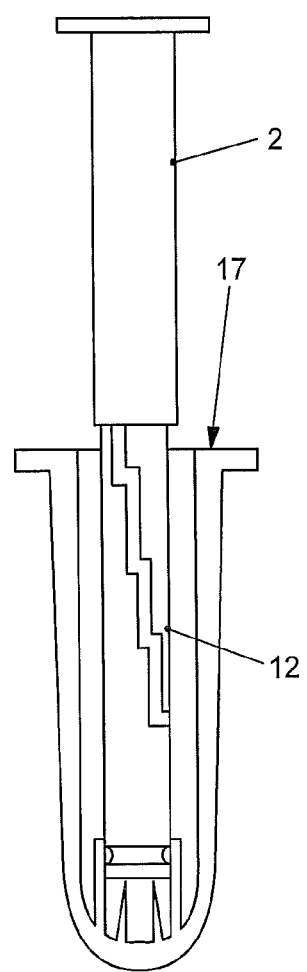
FIG. 4 a further embodiment of a pre-fill syringe in accordance with the invention.

FIG. 4 shows another embodiment. Here shown are the receiver tube 12 in a simplified manner and the piston 2 in functional state. It can also be discerned how almost over the whole area of the receiver tube 12 an adaption 17 is mounted. This embodiment is meant to make clear that the device in accordance with the invention is designed such that it can also be utilized with conventional adaptations, as employed, for example, in vaginal use.

Figure 5:
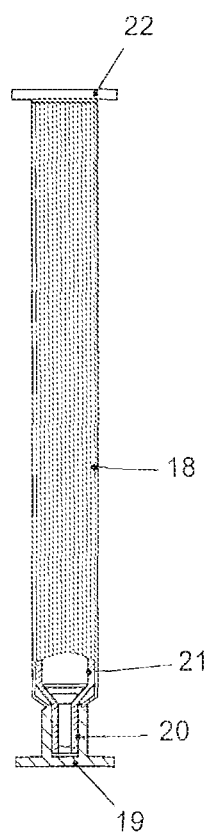
FIG. 5 an embodiment of another pre-fill syringe in accordance with the invention in transport state.

FIG. 5 shows a further embodiment of a pre-fill syringe in accordance with the invention. There shown are a piston 18 as well as a lid 19. The lid 19 closes the nozzle 20 of the receiving tube 21, which in FIG. 5 is shown only partially as a cutaway illustration. Additionally, the receiving tube 21 at its upper end is formed to include a ring 22.

Figure 6:
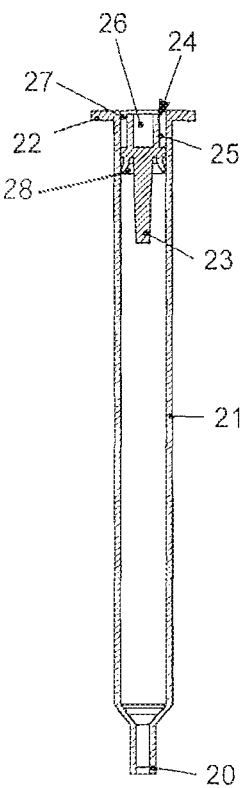
FIG. 6 a cutaway side view of a receiving tube from FIG. 5.

As clearly seen in FIG. 6, the hollow receiving tube 21 has an internal surface which is sealed by seal member 24. The seal member 24 comprises at a first end portion an extension member 23 adapted to penetrate the nozzle 20 of the receiving tube. The seal member further includes a second middle portion comprising a peripheral ring member 28 having an outer surface adapted to seal against the internal circumferential surface of the hollow receiving tube 21. The seal member 24 at the other end portion has a hollow rim portion having a circular recess 26 and a rim extension 25 which defines with the internal circumferential surface of the receiving tube 21 a receiving chamber 27. The piston 18 is adapted to be received in at least one of the receiving chamber 27 and/or recess 26 for moving the seal member 24 in the tube 21 to the nozzle 20 where the extension member 23 penetrates the nozzle 20.

Figure 7:
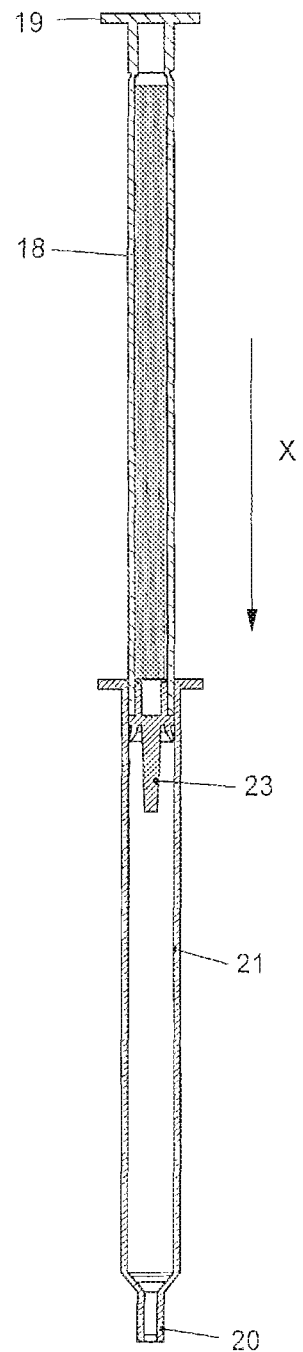
FIG. 7 a pre-fill syringe in accordance with the invention in functional state.

Now, in FIG. 7 it is shown how the piston 18 has been drawn off of the receiving tube 21. Subsequently, lamellar exterior membrane of the piston 18 now fits either into the receiving chamber 27 or even into the recess 26 of the sealing 27.

Now, the closure 19 serves to press the piston 18 in the direction of the arrow X and simultaneously to shove the sealing 23 towards the nozzle 20. Through this process, a fluid in the receiving tube 21 through the sealing 23 out of the nozzle 20.

Figure 8:
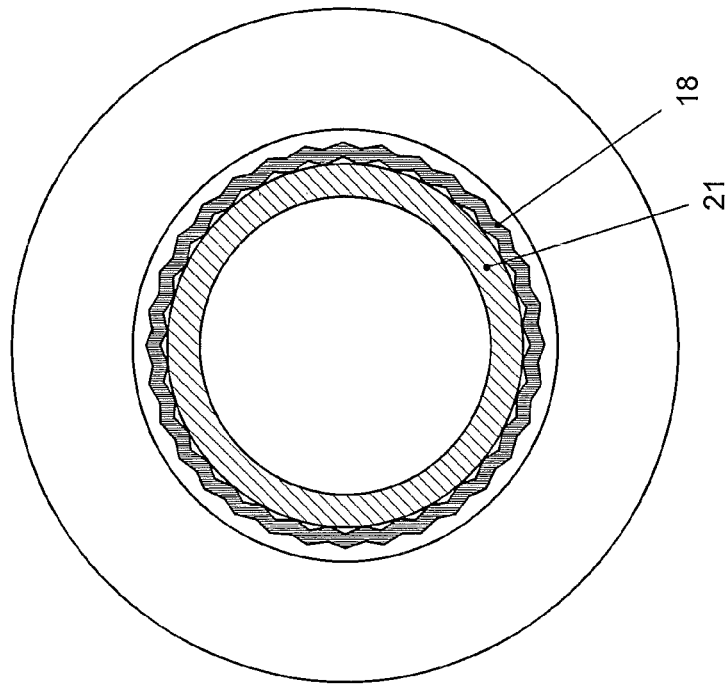
FIG. 8 a cutaway transverse view of FIG. 5.

FIG. 8 shows once more how the piston 18 possessing a greater circumference is shoved over the receiving tube 21.

Figure 9:
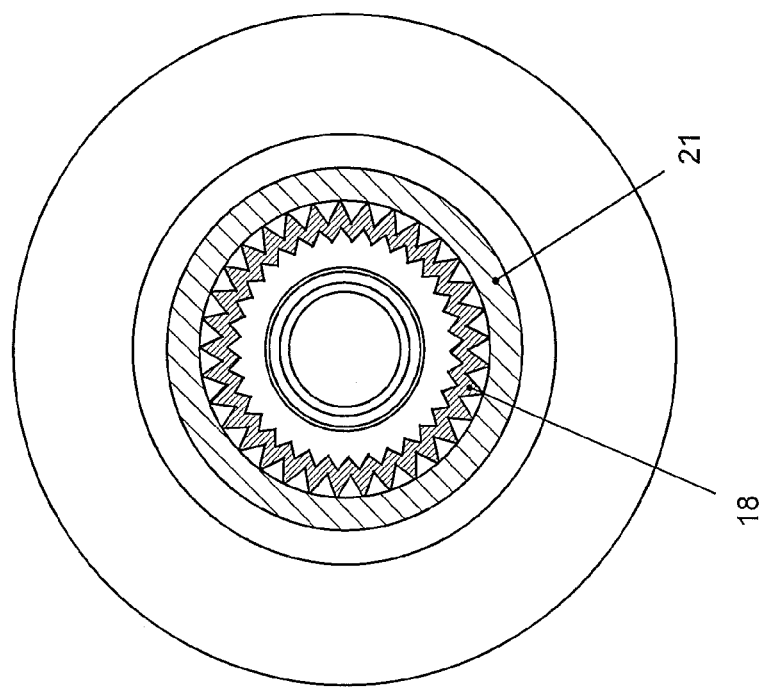
FIG. 9 a cutaway transverse view of FIG. 7.

FIG. 9 shows how the piston 18 with a reduced circumference is positioned inside the receiving tube 21 and can be moved along the inner membrane of the receiving tube 21.

The invention claimed is:

1. A pre-fill syringe comprising:
   a receiving tube defining a chamber for receiving and accommodating a pre-fill medium, the receiving tube having an inner circumferential surface and including a nozzle at one end region of the receiving tube;
   a seal member provided in the receiving tube at an opposite end region of the receiving tube, the seal member being movable within the tube and sealing against the inner circumferential surface; and
   a piston configured to engage with the seal member during use to move the seal member within the receiving tube from said other end region of the tube towards the nozzle, wherein a circumference of the piston is variable by a user such that the circumference of at least part of the piston is configured to be expanded and compressed by the user to move the piston between an expanded state, in which the piston is configured to encompass and surround the receiving tube in a manner of a sheath during transport, and a compressed state for moving the seal member within the receiving tube during use.

2. The pre-fill syringe according to claim 1, wherein the circumference of the piston is folded in a concertina-like or bellows-like manner for movement between the expanded state during transport and the compressed state during use.

3. The pre-fill syringe according to claim 1, wherein the piston comprises a flexible membrane.

4. The pre-fill syringe according to claim 1, wherein the piston is received within the receiving tube as it is pushed during use to move the seal member towards the nozzle.

5. The pre-fill syringe according to claim 1, wherein the seal member has a coupling at a first end portion which is configured to inter-engage or connect with the piston during use.

6. The pre-fill syringe according to claim 1, wherein the seal member has a middle portion comprising a peripheral ring member having an outer surface adapted to seal against the internal circumferential surface of the receiving tube.

7. The pre-fill syringe according to claim 1, wherein the seal member has an extension member at a second end portion thereof which is adapted to penetrate into the nozzle.

8. The pre-fill syringe according to claim 1, wherein the receiving tube includes a peripheral flange at the opposite end region of the receiving tube.

9. The pre-fill syringe according to claim 1, wherein the receiving tube includes a longitudinally extending groove formed in the inner circumferential surface.

10. The pre-fill syringe according to claim 9, wherein the piston includes a curved cam which is formed to fit into and function together with the groove during use.

11. The pre-fill syringe according to claim 1, comprising a cap configured to cover the nozzle of the tube during transport.

12. The pre-fill syringe according to claim 11, wherein the cap is removable from the nozzle and configured for attachment to the piston for actuating the piston during use.

13. The pre-fill syringe according to claim 1, the piston being configured to be inserted over the nozzle to encompass and surround the receiving tube in a manner of a sheath during transport.

14. A pre-fill syringe comprising:
a hollow receiving tube defining a chamber for accommodating a pre-fill medium, the receiving tube having an inner circumferential surface and including a nozzle at one end region of the receiving tube;
a seal member provided in the receiving tube at an opposite end region of the receiving tube, the seal member being movable within the tube and sealing against the inner circumferential surface; and
a piston configured to engage with the seal member during use to move the seal member within the receiving tube from said other end region of the tube towards the nozzle,
wherein a circumference of the piston is variable by a user such that the circumference of at least part of the piston is configured to be expanded and compressed by the user to move the piston between an expanded state, in which the piston is configured to be inserted over said one end region of the hollow receiving tube to encompass and surround the hollow receiving tube during transport, and a compressed state for moving the seal member within the receiving tube during use.

15. The pre-fill syringe according to claim 14, wherein the circumference of the piston is folded in a concertina-like or bellows-like manner for movement between an expanded state during transport and a compressed state during use.

16. The pre-fill syringe according to claim 14, wherein the piston comprises a flexible membrane.

* * * * *